US009662493B2

United States Patent
Kals et al.

(10) Patent No.: US 9,662,493 B2
(45) Date of Patent: May 30, 2017

(54) AUTOMATIC FITTING-MAPPING-TRACKING BASED ON ELECTRODE IMPEDANCES IN COCHLEAR IMPLANTS

(71) Applicant: MED-EL Elektromedizinische Geraete GmbH, Innsbruck (AT)

(72) Inventors: Mathias Kals, Innsbruck (AT); Ernst Kabot, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/660,246

(22) Filed: Mar. 17, 2015

(65) Prior Publication Data

US 2015/0265838 A1  Sep. 24, 2015

Related U.S. Application Data

(60) Provisional application No. 61/955,399, filed on Mar. 19, 2014.

(51) Int. Cl.
*A61N 1/00* (2006.01)
*A61N 1/36* (2006.01)
*A61N 1/05* (2006.01)

(52) U.S. Cl.
CPC ........ *A61N 1/36032* (2013.01); *A61N 1/0541* (2013.01)

(58) Field of Classification Search
USPC .................................................. 607/57, 137
See application file for complete search history.

(56) References Cited

U.S. PATENT DOCUMENTS

| 6,157,861 | A * | 12/2000 | Faltys ................ A61N 1/36032 |
| | | | 607/57 |
| 6,366,676 | B1 | 4/2002 | Neilson ......................... 381/314 |
| 8,761,871 | B2 * | 6/2014 | Blomqvist ........... A61B 5/0537 |
| | | | 600/547 |
| 2011/0087085 | A1 | 4/2011 | Tsampazis et al. ........... 600/379 |
| 2011/0098786 | A1 | 4/2011 | Mishra et al. .................. 607/57 |
| 2012/0202371 | A1 | 8/2012 | Portmann et al. ............ 439/374 |

(Continued)

OTHER PUBLICATIONS

Mens, PhD, "Advances in Cochlear Implant Telemetry: Evoked Neural Responses, Electrical Field Imaging, and Technical Integrity," Trends in Amplification, vol. 11, No. 3, pp. 143-159, Sep. 2007.

(Continued)

*Primary Examiner* — Nicole F Johnson
*Assistant Examiner* — Nicole F. Lavert
(74) *Attorney, Agent, or Firm* — Sunstein Kann Murphy & Timbers LLP

(57) ABSTRACT

A system, method, and computer product for adjusting dynamic range of electrical stimulation associated with a cochlear prosthesis system is provided. The cochlear prosthesis system includes an electrode array for stimulating the acoustic nerve. Present electrode impedance values are determined for an electrode in the array. At least one stimulation parameter for the electrode is adjusted based, at least in part, on the present electrode impedance values, such that hearing sensation is not influenced due to a change between the present electrode impedance values and previous electrode impedance values.

41 Claims, 5 Drawing Sheets

(56) References Cited

U.S. PATENT DOCUMENTS

2013/0243228 A1   9/2013  Müller ........................ 381/315
2013/0282077 A1* 10/2013  Saoji ................. A61N 1/36032
                                                             607/57

OTHER PUBLICATIONS

Vanpoucke et al., "The Facial Nerve Canal: An Important Cochlear Conduction Path Revealed by Clarion Electrical Field Imaging," Otology & Neurotology, vol. 25, pp. 282-289, Nov. 3, 2004.
International Searching Authority, International Search Report—International Application No. PCT/US2015/021064, dated Jun. 22, 2015, together with the Written Opinion of the International Searching Authority, 21 pages.

* cited by examiner

AUTOMATIC FITTING-MAPPING-TRACKING BASED ON ELECTRODE IMPEDANCES IN COCHLEAR IMPLANTS

CROSS-REFERENCE TO RELATED APPLICATIONS

This application claims priority from U.S. provisional patent application Ser. No. 61/955,399 filed Mar. 19, 2014, entitled "Automatic Fitting-Mapping-Tracking based on Electrode Impedances in Cochlear Implants," which is hereby incorporated herein by reference in its entirety.

TECHNICAL FIELD

The present invention relates to an implantable hearing prosthesis, and more particularly to automatic fitting, mapping and/or tracking based on measured electrode impedances of a cochlear implant.

BACKGROUND ART

Cochlear implants (CIs) and other inner ear prostheses are one option to help profoundly deaf or severely hearing impaired persons. Unlike conventional hearing aids that just apply an amplified and modified sound signal; a cochlear implant is based on direct electrical stimulation of the acoustic nerve. Typically, a cochlear implant stimulates neural structures in the inner ear electrically in such a way that hearing impressions most similar to normal hearing is obtained.

A normal ear transmits sounds as shown in FIG. 1 through the outer ear 101 to the tympanic membrane (eardrum) 102, which moves the bones of the middle ear 103 (malleus, incus, and stapes) that vibrate the oval window of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Some persons have partial or full loss of normal sensorineural hearing. Cochlear implant systems have been developed to overcome this by directly stimulating the user's cochlea 104. A typical cochlear prosthesis may include two parts: the audio processor 111 and the implanted stimulator 108. The audio processor 111 typically includes a microphone, a power supply (batteries) for the overall system and a processor that is used to perform signal processing of the acoustic signal to extract the stimulation parameters. The audio processor 111 may be an external behind-the-ear (BTE-) device, may be a single unit that integrates the processor, battery pack and coil (e.g., the RONDO Single Unit processor from MED-EL Elektromedizinische Geraete GmbH) or may be implantable.

The stimulator 108 generates the stimulation patterns (based on the extracted audio information) that is sent through an electrode lead 109 to an implanted electrode array 110. Typically, this electrode array 110 includes multiple electrodes on its surface that provide selective stimulation of the cochlea 104. For example, each electrode of the cochlear implant is often stimulated with signals within an assigned frequency band based on the organization of the inner ear. The assigned frequency band of an electrode is typically based on its placement within the cochlea, with electrodes closer to the base of the cochlea generally corresponding to higher frequency bands.

The connection between a BTE audio processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

For optimal hearing performance, repeated adjustment of strategy-related map parameters, that are used for programming a cochlear implant prosthesis system to the specifications and needs of its user may be performed from time to time. This is especially true for the electric dynamic range (DR), which is defined by the maximum comfortable loudness (MCL) and threshold (THR)-charge level for each electrode, and which influences performance strongly. The MCL indicates the level at which perceived sound is loud but comfortable; while the THR typically indicates the threshold of hearing. Typically, an increase in MCL or M-level stimulation amplitudes has been found during the first year post implantation, while at the same time electrode impedance values (EIVs) decrease. Usually, stabilization of stimulation levels and EIVs occurs after approximately three months.

In clinical routine, the map parameters are usually adjusted in several sessions by an audiologist on a fixed schedule. Additional visits may be necessary if a CI patient complains about dysfunction or non-optimal functionality of the CI system.

Commonly, progressive maps are used for the run-in period, i.e., during the first few months, several maps with progressively increasing MCL amplitudes (by a certain percentage) are generated. The CI patient is instructed by the clinician to manually switch between these maps. With progressive maps, the anticipated charge increase that may occur during this time period may be managed without additional clinical visits. Unfortunately, progressive maps comprise the risk of over-stimulation, for example, if created maps can not be activated at the time of map creation due to the involved charge values exceeding the actual dynamic range of the patient.

Since both the course of map stabilization and the optimal re-fitting intervals vary individually from patient to patient, no optimal universal time schedule can be defined. Generally, short visit intervals to the clinic may improve listening performance in some patients, but will also lead to higher workload for clinics. Furthermore, more frequent visits to the clinics may be unreasonable due to the often considerable travelling, time and cost burdens placed on the patient.

SUMMARY OF THE EMBODIMENTS

In accordance with an embodiment of the invention, there is provided a method of adjusting dynamic range of electrical stimulation associated with a cochlear prosthesis system. The cochlear prosthesis system includes an electrode array for stimulating the acoustic nerve. The method includes determining present electrode impedance values for an electrode in the array. At least one stimulation parameter for the electrode is adjusted based, at least in part, on the present electrode impedance values, such that hearing sensation is not influenced due to a change between the present electrode impedance values and previous electrode impedance values.

In accordance with related embodiments of the invention, the electrode array may have a monopolar configuration, or alternatively, a bipolar configuration. The at least one stimulation parameter may be a Most Comfortable Level (MCL) parameter, a Threshold (THR) parameter, and/or an electric dynamic range (DR). Adjusting the at least one stimulation parameter may include maintaining charge $Q_{Ti}$ that stimulates the acoustic nerve constant. Adjusting the at least one stimulation parameter may include adjusting pulse duration of stimulation current $I_i$ provided to the electrode. Adjusting the at least one stimulation parameter may be a function of both longitudinal tissue impedance $Z_L$ between electrodes, and transversal tissue impedance $Z_T$. Adjusting the at least one stimulation parameter may include adjusting stimulation current level $I_i$ provided to the electrode upon an increase in longitudinal impedance $Z_L$. The steps of determining and adjusting may be repeated for each electrode in the array. A weighting may be used to take into account spatial channel interaction. Determining current electrode impedance values may include determining tissue impedances $Z_{Ti}$, $Z_{Ai}$, and $Z_{Bi}$.

In accordance with other related embodiments of the invention, the cochlear prosthesis system may include an audio processor for converting an incoming acoustic signal into an encoded signal, and a stimulation module for providing stimulation signals to the electrode array as a function of the encoded signal received from the audio processor. The determining and adjusting is automatically performed within the audio processor or the stimulation module, or a combination thereof.

In accordance with further related embodiments of the invention, the method may include coupling an external fitting processor to an audio processor of the cochlear prosthesis system, wherein the determining and adjusting is performed, at least in part, at the external fitting processor.

In accordance with another embodiment of the invention, a cochlear prosthesis system includes an electrode array configured to stimulate the acoustic nerve. An audio processor is configured to convert an incoming acoustic signal into an encoded signal. A stimulator is configured to provide stimulation signals to the electrode array as a function of the encoded signal received from the audio processor. A dynamic range adjustment module is configured to determine present electrode impedance values for an electrode in the array, and further configured to adjust at least one stimulation parameter for the electrode based, at least in part, on the present electrode impedance values, such that hearing sensation is not influenced due to a change between the present electrode impedance values and previous electrode impedance values.

In accordance with related embodiments of the invention, the electrode array may have a monopolar configuration, or alternatively, a bipolar configuration. The dynamic range adjustment module may be positioned, at least in part, within the audio processor or the stimulation module, or a combination thereof. The dynamic range adjustment module may be configured to automatically adjust the at least one stimulation parameter. An external fitting processor may be configured to operatively couple to the audio processor, wherein the dynamic range adjustment module may be positioned, at least in part, within the external fitting processor.

In accordance with other related embodiments of the invention, the at least one stimulation parameter may be a Most Comfortable Level (MCL) parameter, a Threshold (THR) parameter, an electric dynamic range (DR), or combinations thereof. The dynamic range adjustment module may be configured to adjust the at least one stimulation parameter so as to maintain charge $Q_{Ti}$ that stimulates the acoustic nerve constant. The dynamic range adjustment module may be configured to adjust the at least one stimulation parameter by adjusting pulse duration of stimulation current $I_i$ provided to the electrode. The dynamic range adjustment module may be configured to adjust the at least one stimulation parameter as a function of both longitudinal tissue impedance $Z_L$ between electrodes, and transversal tissue impedance $Z_T$. The dynamic range adjustment module may be configured to adjust stimulation current level $I_i$ provided to the electrode upon an increase in longitudinal impedance $Z_L$. The dynamic range adjustment module may be configured to determine tissue impedances $Z_{Ti}$, $Z_{Ai}$, and $Z_{Bi}$.

In accordance with another embodiment of the invention, a cochlear prosthesis system includes an electrode array for stimulating the acoustic nerve. The system further includes means for determining present electrode impedance values for an electrode in the array. The system further includes means for adjusting at least one stimulation parameter for the electrode based, at least in part, on the present electrode impedance values, such that hearing sensation is not influenced due to a change between the present electrode impedance values and previous electrode impedance values.

In accordance with related embodiments of the invention, the electrode array may have a monopolar configuration, or alternatively, a bipolar configuration. The at least one stimulation parameter may include a Most Comfortable Level (MCL) parameter, a Threshold (THR) parameter, or an electric dynamic range (DR), or combinations thereof. The means for adjusting the at least one stimulation parameter may include means for maintaining charge $Q_{Ti}$ that stimulates the acoustic nerve constant. The means for adjusting the at least one stimulation parameter may include means for adjusting pulse duration of stimulation current $I_i$ provided to the electrode. The means for adjusting the at least one stimulation parameter may include means for adjusting the at least one stimulation parameter as a function of both longitudinal tissue impedance $Z_L$ between electrodes, and transversal tissue impedance $Z_T$. The means for adjusting the at least one stimulation parameter may adjust stimulation current level $I_i$ provided to the electrode upon an increase in longitudinal impedance $Z_L$. The means for determining current electrode impedance values may include means for determining tissue impedances $Z_{Ti}$, $Z_{Ai}$, and $Z_{Bi}$.

In accordance with related embodiments of the invention, the system may further include an audio processor for converting an incoming acoustic signal into an encoded signal. A stimulation module provides stimulation signals to an electrode array as a function of the encoded signal received from the audio processor. The means for determining and the means for adjusting is automatically performed within the audio processor or the stimulation module, or a combination thereof.

In accordance with further related embodiments of the invention, the system may further include an audio processor for converting an incoming acoustic signal into an encoded signal. A stimulation module provides stimulation signals to an electrode array as a function of the encoded signal received from the audio processor. An external fitting processor is coupled to the audio processor. The means for determining and the means for adjusting is performed, at least in part, at the external fitting processor.

In accordance with another embodiment of the invention, a computer program product for adjusting dynamic range of electrical stimulation associated with a cochlear prosthesis system is provided. The cochlear prosthesis system includes an electrode array for stimulating the acoustic nerve, the electrode array having a monopolar electrode configuration. The computer program product includes a non-transitory computer usable medium having computer readable program code thereon. The computer readable program code includes program code for determining present electrode impedance values for an electrode in the array.

In accordance with related embodiments of the invention, the electrode array may have a monopolar configuration, or alternatively, a bipolar configuration. The at least one stimulation parameter may be a Most Comfortable Level (MCL) parameter, a Threshold (THR) parameter, or an electric dynamic range (DR), or combinations thereof. The program code for adjusting the at least one stimulation parameter may include program code for maintaining charge $Q_{Ti}$ that stimulates the acoustic nerve constant. The program code for adjusting the at least one stimulation parameter may include program code for adjusting pulse duration of stimulation current $I_i$ provided to the electrode. The program code for adjusting the at least one stimulation parameter may include program code for adjusting the at least one stimulation parameter as a function of both longitudinal tissue impedance $Z_L$ between electrodes, and transversal tissue impedance $Z_T$. The program code for adjusting the at least one stimulation parameter may include program code for adjusting stimulation current level $I_i$ provided to the electrode upon an increase in longitudinal impedance $Z_L$. The program code for determining current electrode impedance values may include program code for determining tissue impedances $Z_{Ti}$, $Z_{Ai}$, and $Z_{Bi}$.

In accordance with further related embodiments of the invention, the cochlear prosthesis system may further include an audio processor for converting an incoming acoustic signal into an encoded signal, and a stimulation module for providing stimulation signals to an electrode array as a function of the encoded signal received from the audio processor. The program code for determining and the program code for adjusting is automatically performed within the audio processor or the stimulation module, or a combination thereof.

In accordance with still further related embodiments of the invention, the cochlear prosthesis system further includes an audio processor for converting an incoming acoustic signal into an encoded signal, a stimulation module for providing stimulation signals to an electrode array as a function of the encoded signal received from the audio processor, and an external fitting processor coupled to the audio processor. The program code for determining and the program code for adjusting is performed, at least in part, at the external fitting processor.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments of the invention, adjustment of the dynamic range used for electrical stimulation of the hearing nerve by a cochlear prosthesis system is provided, which may be automatically performed. The adjustment may ensure, for example, that changes to electrode impedance values (EIVs) occurring after the fitting of a map, will not influence the hearing sensation of a cochlear implant user. Implementation of the adjustment into the audio processor or implanted stimulator of the cochlear prosthesis system may ensure that corrections are immediately performed, independent from the patient's regular visits to the supervising clinic, leading to fewer overall fitting visits for cochlear implant (CI) patients and reducing workload on clinics. Additionally, an alarm management may be incorporated. For example, if measured EIV changes or desired charge adjustments exceed a certain level, the cochlear prosthesis system may alert the patient to visit the clinic. Details are discussed below.

Figure 2:
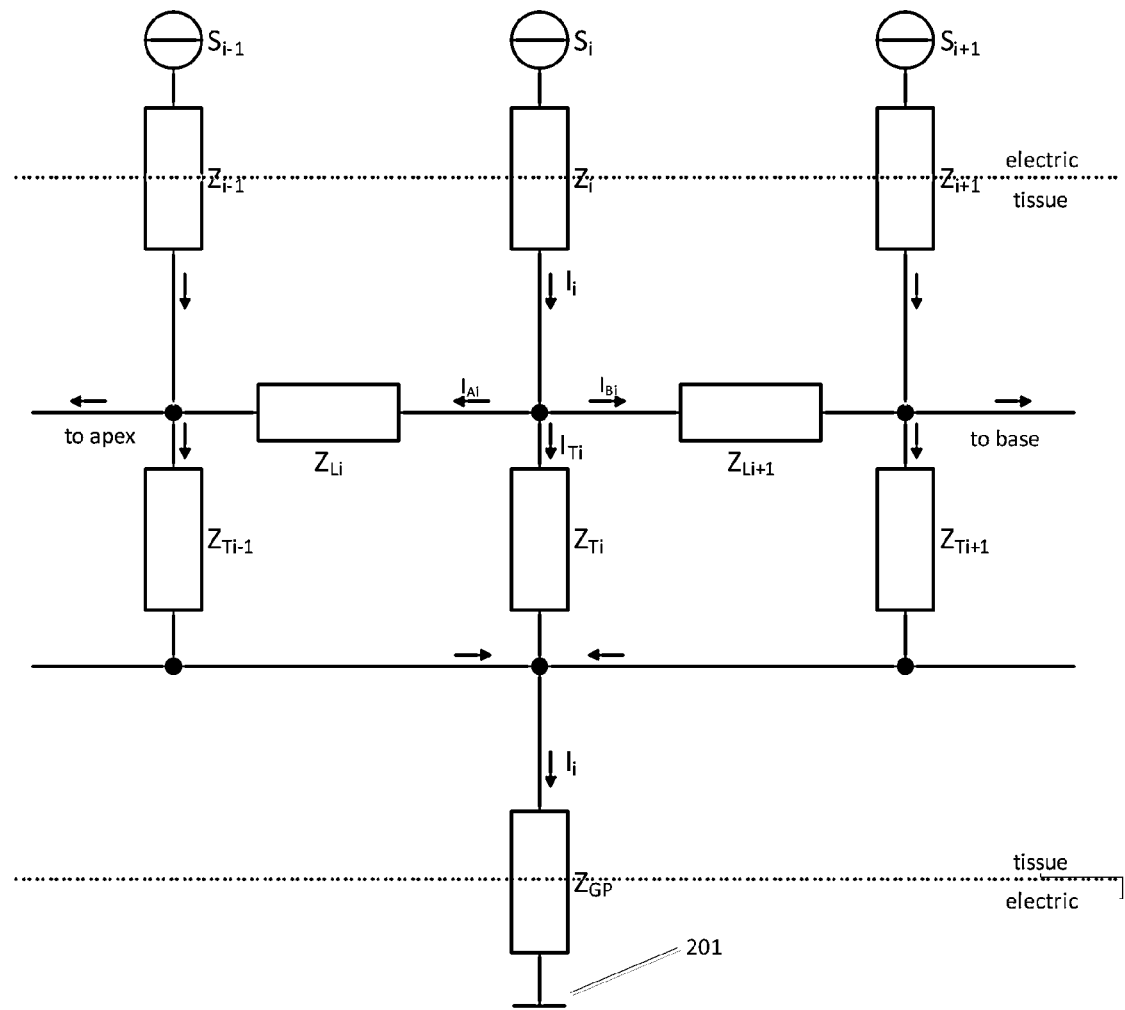
FIG. 2 shows a schematic model of the current flow inside the cochlear caused by electric stimulation of a cochlear prosthesis system using a simplified resistor network, in accordance with an embodiment of the invention.

FIG. 2 shows a schematic model of the current flow inside the cochlear caused by electric stimulation of a cochlear prosthesis system using a simplified resistor network, in accordance with an embodiment of the invention. The cochlear prosthesis system in FIG. 2 includes an electrode array for stimulating the acoustic nerve. The electrode array has, without limitation, a monopolar electrode configuration with a reference electrode 201, positioned outside the cochlear, however it is to be understood that other electrode configurations known in that art allowing for monopolar stimulation may be utilized, and having one or more reference electrodes 201 outside the cochlear. Furthermore, as described in further below embodiments, the electrode array may have a bipolar configuration.

An active current source $S_i$ of a cochlear implant produces stimulation current $I_i$ that enters the cochlear by passing the interface impedance $Z_i$ at the corresponding electrode contact i∈{1, . . . , N}. Then, the current flows through cochlear and extra-cochlear tissue towards the reference electrode 201 and finally passes the reference electrode interface impedance $Z_{GP}$.

In the network shown in FIG. 2, the stimulation current $I_i$ is divided into the longitudinal and transversal components $I_{Ai}$, $I_{Bi}$, and $I_{Ti}$. The longitudinal components $I_{Ai}$ and $I_{Bi}$ represent the current flow along the electrode array 101 inside the cochlear towards apex and base. They allow the determination of longitudinal tissue impedances $Z_L$ between electrode contacts within the cochlear. For example $Z_{Li+1}$ stands for the tissue impedance between electrode contact i and electrode contact i+1. The transversal component $I_{Ti}$ represents the portion of current that leaves scala tympani through the bony wall and contributes to the electric stimulation of the hearing nerve. $Z_{Ti}$ accounts for the impedance of this path.

Figure 3:
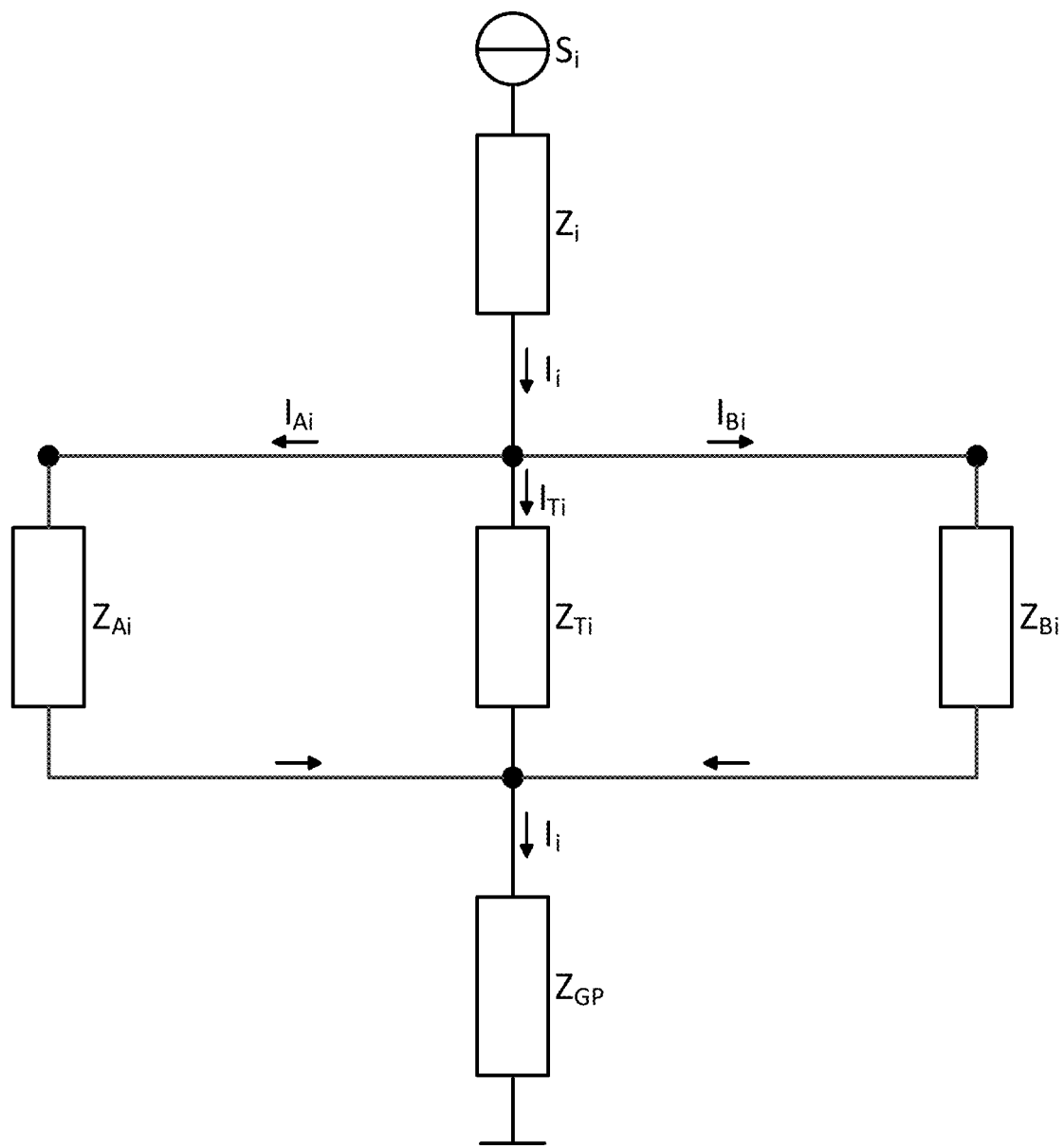
FIG. 3 shows current flow inside the cochlear caused by electric stimulation, modeled by a simplified resistor network acting as a current divider, in accordance with an embodiment of the invention.

The network can be reduced even more, as shown in FIG. 3, in accordance with an embodiment of the invention. FIG. 3 shows current flow inside the cochlear caused by electric stimulation, modeled by a simplified resistor network acting as a current divider, in accordance with an embodiment of the invention. All tissue impedances located towards the apex, i.e., longitudinal and transversal ones, are replaced by the equivalent impedance $Z_{Ai}$. The same holds true for all tissue impedances located towards the base of the cochlear, which are replaced by the equivalent impedance $Z_{Bi}$.

Together, the three impedances $Z_{Ti}$, $Z_{Ai}$, and $Z_{Bi}$ build a current divider. Any change in longitudinal or transverse tissue impedances, either in the main stimulation path $Z_{Ti}$ or in the apical or basal paths $Z_{Ai}$ or $Z_{Bi}$, will cause a variation to the current divider, which as a result will change the ratio of current components $I_{Ai}$, $I_{Bi}$, and $I_{Ti}$.

With time, the interface between the electrode surface of an electrode array and the cochlear fluid will change, resulting in a change of EIVs. Also tissue alteration inside the cochlea will cause impedance variations. Without re-adjustment, these impedance changes will alter the charge $Q_{Ti}$ that stimulates the acoustic nerve and will finally lead to a variation in hearing sensation.

In various embodiments, a comparison of actual EIVs and EIVs from the time of a previous fitting/mapping will clearly show the change in impedances, and may be used as the basis for compensating these changes and thus restoring the prior hearing perception. Based on the measured EIVs, map-tracking of stimulation parameters may be performed, in which mapping parameters are advantageously automatically adjusted. For example, at least one stimulation parameter may be adjusted so as to maintain the charge $Q_{Ti}$ that stimulates the acoustic nerve constant. For simplicity, in various below-described embodiments, adjustments to stimulation currents or pulse duration are discussed ($Q_{Ti}$ is the product of current and pulse duration), however it is to be understood that any stimulation parameters may be adjusted, so as to maintain charge $Q_{Ti}$ that stimulates the acoustic nerve constant, in accordance with various embodiments of the invention.

Illustratively, as the electric stimulation of the hearing nerve is strongly related to the currents $I_{Ti}$, any change to the current divider in FIG. 3 may be compensated by automatic adjustment. For example, the current $I_{Ti}$ may be, without limitation, corrected to reflect its prior and/or last value. Re-adjusting $I_{Ti}$ will restore the prior percept of a map, defined, for example, without limitation, by the dynamic range, MCLs and/or THRs, thus avoiding noticeable changes in hearing sensation.

Determination of the impedances $Z_{Ti}$, $Z_{Ai}$, and $Z_{Bi}$ and thus the current divider may be performed with the help of measured EIVs. With knowledge of the currents $I_{Ti}$ at the time of map creation, any deviation $dI_{Ti}$ may be compensated by an appropriate adjustment of the overall currents $I_i$.

The following example illustrates various calculations that may be used, in accordance with various embodiments of the invention.

At the time of a map creation $t_0$, the following impedances may be determined $Z_{Ti}(t_0)=40$ k$\Omega$ $Z_{Ai}(t_0)=10$ k$\Omega$ $Z_{Bi}(t_0)=10$ k$\Omega$.

This results in a current ratio of:

$$\frac{I_{Ti}(t_0)}{I_i(t_0)} = \frac{\frac{1}{\frac{1}{Z_{Ai}(t_0)} + \frac{1}{Z_{Ti}(t_0)} + \frac{1}{Z_{Bi}(t_0)}}}{Z_{Ti}(t_0)} = 0.11$$

In this case actually only 11% of the applied current $I_i$ passes $Z_{Ti}$.

At a later time $t_1$, the impedances may have changed to:

$Z_{Ti}(t_1)=40$ k$\Omega$ $Z_{Ai}(t_1)=12$ k$\Omega$ $Z_{Bi}(t_1)=12$ k$\Omega$.

A determination of this current ratio leads to:

$$\frac{I_{Ti}(t_1)}{I_i(t_1)} = \frac{\frac{1}{\frac{1}{Z_{Ai}(t_1)} + \frac{1}{Z_{Ti}(t_1)} + \frac{1}{Z_{Bi}(t_1)}}}{Z_{Ti}(t_1)} = 0.13$$

A factor $A_i$ may be used to express the proportion of $I_{Ti}$ at time $t_1$ in comparison to time $t_0$, if the same stimulation currents are used [$I_i(t_1)=I_i(t_0)$]. In this example, this would lead to:

$$A_i = \frac{I_{Ti}(t_0) * I_i(t_1)}{I_{Ti}(t_1) * I_i(t_0)} = \frac{0.11}{0.13} = 0.85$$

Illustratively, to keep the current $I_{Ti}$ at tissue impedance $Z_{Ti}$ constant [$I_{Ti}(t_1)=I_{Ti}(t_0)$] as the primary goal, the overall stimulation current $I_i$ would be $I_i=I_i(t_0)*A_i$.

A new map may thus be calculated accordingly by:

$MCL_i=A_i*MCL_i(t_0)$ $THR_i=A_i*THR_i(t_0)$

The above-described determination of adjustments may be repeated for all or a subset of the electrodes associated with the cochlear implant prosthesis, resulting in a set of compensation parameters for the whole map, dedicated to re-adjust any impedance change with respect to the underlying map.

Adjustments of the currents delivered to individual electrodes can also influence the overall spread of excitation and thus might also impact on the hearing sensation. Therefore, an optimization algorithm may be used to determine the ideal set of re-adjustment parameters and to restore the prior current distribution at the hearing nerve as best as possible. Generally, the strength of the hearing sensation is monotonically increasing with increasing stimulation current (until to a certain upper limit). To ensure a minimum change in hearing perception, a weighting may be used to minimise errors at electrodes spatially adjacent to the stimulating one.

As stimulation of the hearing nerve is approximately proportional to the applied charge, the re-adjustments described above, which may be automatic, may adjust stimulation current pulse duration instead of, or in combination with, adjustment of the stimulation current amplitude.

Figure 4:
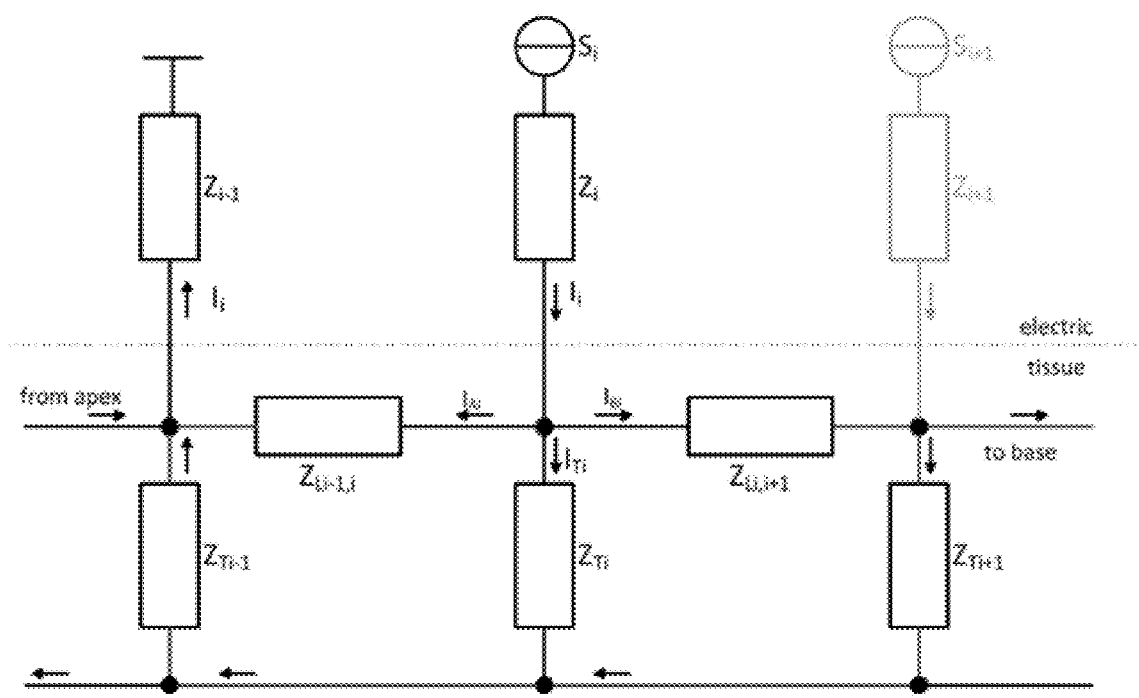
FIG. 4 shows a schematic model of the current flow inside the cochlear caused by electric stimulation of a cochlear prosthesis system using a simplified resistor network, with the electrode array having a bipolar electrode configuration, in accordance with an embodiment of the invention.
Figure 5:
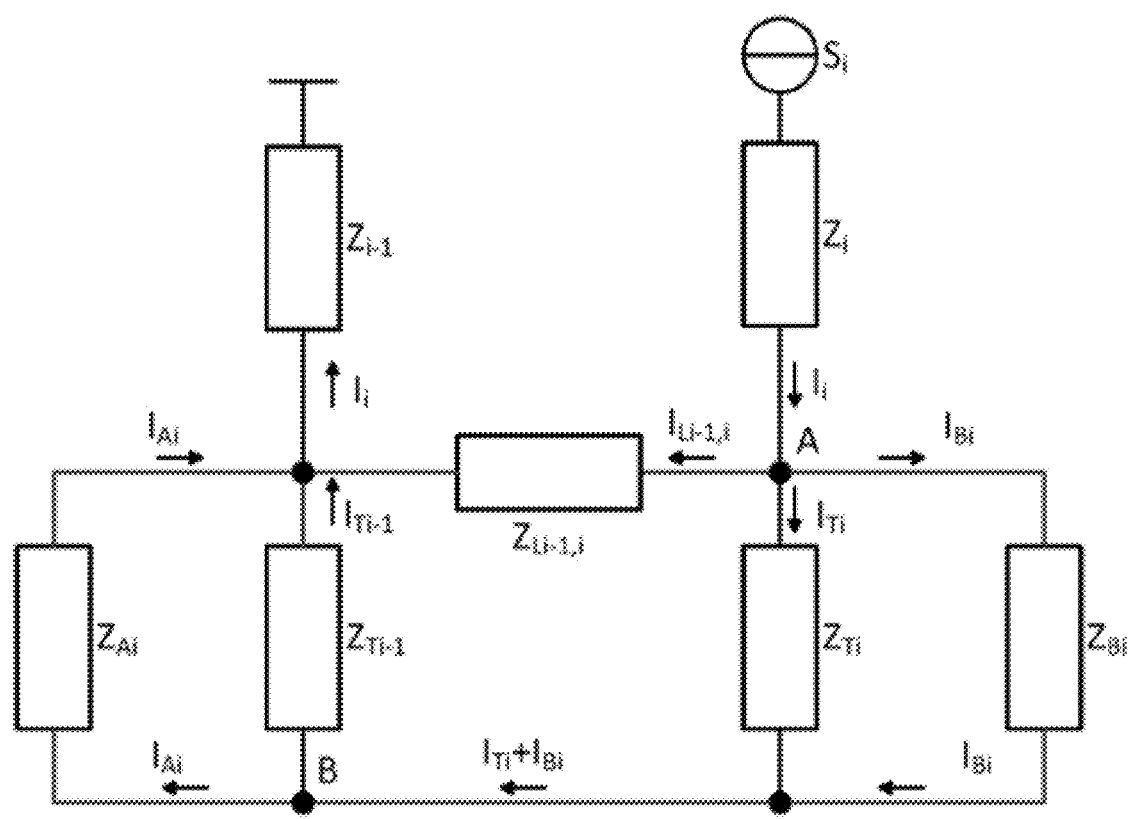
FIG. 5 shows the network of FIG. 4 reduced even more, in accordance with an embodiment of the invention.

FIG. 4 shows a schematic model of the current flow inside the cochlear caused by electric stimulation of a cochlear prosthesis system using a simplified resistor network, with the electrode array having a bipolar electrode configuration, in accordance with an embodiment of the invention. FIG. 5 shows the network of FIG. 4 reduced even more, in accordance with an embodiment of the invention.

The subnetwork of $Z_{Ai}$, $Z_{Bi}$, and $Z_{Ti-1}$ in FIG. 5 may be replaced by Z':

$$Z' = \frac{Z_{Ti} * Z_{Bi}}{Z_{Ti} + Z_{Bi}} + \frac{Z_{Ti-1} * Z_{Ai}}{Z_{Ti-1} + Z_{Ai}}.$$

The subcurrent I', that flows through Z' may be calculated by:

$$\frac{I_{Li-1,i}}{I'} = \frac{Z'}{Z_{Li-1,i}}.$$

With $I_{Li-1,i} = I_i - I'$, I' may be expressed as:

$$I' = I_i * \frac{Z_{Li-1,i}}{Z' + Z_{Li-1,i}}.$$

Finally, the subcurrents $I_{Ti}$ and $I_{Ti-1}$ that we are interested in, are given by:

$$\frac{I_{Bi}}{I_{Ti}} = \frac{Z_{Ti}}{Z_{Bi}}.$$

With $I_{Bi} = I' - I_{Ti}$, $I_{Ti}$ can be expressed as:

$$I_{Ti} = I' * \frac{Z_{Bi}}{Z_{Ti} + Z_{Bi}}$$

$$I_{Ti} = I_i * \frac{Z_{Li-1,i}}{Z' + Z_{Li-1,i}} * \frac{Z_{Bi}}{Z_{Ti} + Z_{Bi}}.$$

The same holds true for $I_{Ti-1}$:

$$I_{Ti-1} = I_i * \frac{Z_{Li-1,i}}{Z' + Z_{Li-1,i}} * \frac{Z_{Ai}}{Z_{Ti-1} + Z_{Ai}}.$$

At the time of a map creation $t_0$, the following impedances may be determined:
$Z_{Ti}(t_0) = 40$ kΩ
$Z_{Ti-1}(t_0) = 40$ kΩ
$Z_{Ai}(t_0) = 10$ kΩ
$Z_{Bi}(t_0) = 11$ kΩ
$Z_{Li-1,i}(t_0) = 1$ kΩ.
Which leads to:

$$\frac{I_{Ti}(t_0)}{I_i(t_0)} = 0.0122,$$

and respective $$\frac{I_{Ti-1}(t_0)}{I_i(t_0)} = 0.00113.$$

At a later time $t_1$, the impedances may have changed to:
$Z_{Ti}(t_1) = 40$ kΩ
$Z_{Ti-1}(t_1) = 40$ kΩ
$Z_{Ai}(t_1) = 12$ kΩ
$Z_{Bi}(t_1) = 14$ kΩ
$Z_{Li-1,i}(t_1) = 1.2$ kΩ.
This leads to:

$$\frac{I_{Ti}(t_1)}{I_i(t_1)} = 0.0150$$

and respective $$\frac{I_{Ti-1}(t_1)}{I_i(t_1)} = 0.0133.$$

Factors $A_i$ and $A_{i-1}$ may be used to express the proportion of $I_{Ti}$ and $I_{Ti-1}$ at time $t_1$ in comparison to time $t_0$, if the same stimulation currents are used [$I_i(t_1) = I_i(t_0)$]. In this example, this would lead to:

$$A_i = \frac{I_{Ti}(t_0) * I_i(t_1)}{I_{Ti}(t_1) * I_i(t_0)} = \frac{0.0122}{00.150} = 0.813$$

$$A_{i-1} = \frac{I_{Ti-1}(t_0) * I_i(t_1)}{I_{Ti-1}(t_1) * I_i(t_0)} = \frac{0.0113}{00.133} = 0.850$$

As both factors show different variations, an optimization algorithm may be used, without limitation, to find the optimum current correction for keeping the modifications of $I_{Ti}$ and $I_{Ti-1}$ as small as possible.

Figure 1:
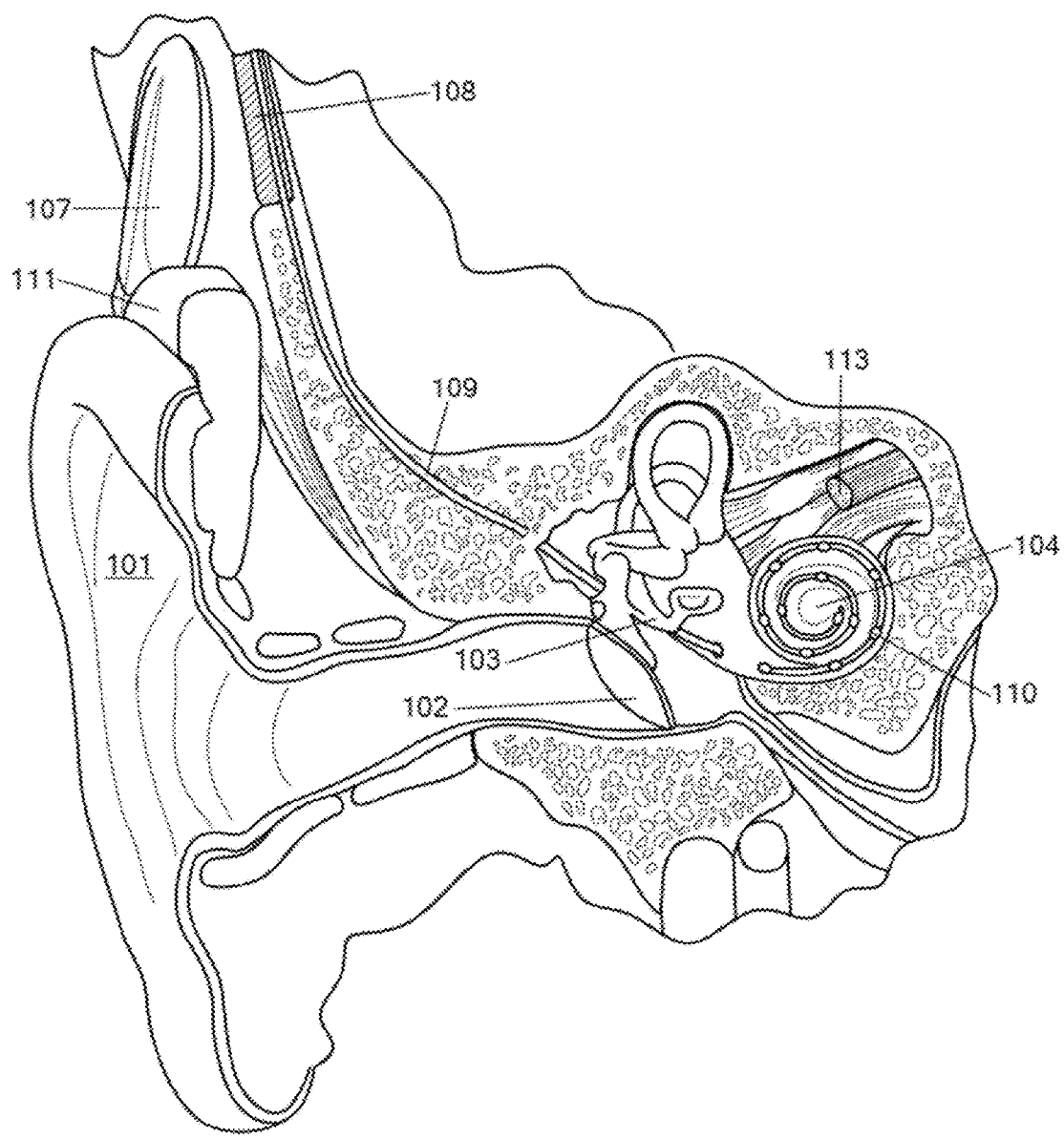
FIG. 1 shows a typical human ear having an acoustic electric hearing implant system.

Referring back to FIG. 1, a cochlear prosthesis system may include at least in part, and without limitation, an audio processor for converting an incoming acoustic signal into an encoded signal, and a stimulation module for providing stimulation signals to the electrode array as a function of the encoded signal received from the audio processor. The above-described adjustments may be performed within the audio processor or the stimulation module, or a combination thereof, without requiring an additional external fitting system. For example, the system may be configured to periodically monitor EIVs, with any adjustments performed automatically without operator intervention. Such automatic re-adjustment ensures that impedance changes, occurring after the fitting of a map, will not influence the hearing sensation of a cochlear implant user. Alternatively, some level of user interaction with the system may be needed. For example, the user may need to initiate and/or confirm any adjustments via a user interface on an external audio processor.

In various embodiments, a cochlear implant fitting system and/or software at least partially separate from the audio processor and stimulation module may, for example, provide recommendations for the map adjustments necessary according to the latest available set of EIVs, whereupon an operator or user may elect to implement the adjustments. Alternatively, the cochlear implant fitting system and/or software may automatically perform the necessary map adjustments.

In various embodiments, an alarm may be provided upon monitoring/detection of impedance changes that may, for example, require a closer investigation by the user and/or clinical personnel. The alarm may be, without limitation, a visual indication, a vibration, an external audio alert, or an audio alert perceived by the user of the cochlear implant based on electrode stimulation of the acoustic nerve.

Implementation of the above-described adjustments into the fitting software, sound processor or implant may advantageously ensure that dynamic range correction is performed in the best way possible, even if performed by a less experienced user/fitter. As a consequence, fewer clinical visits for patients may be necessary.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention.

What is claimed is:

1. A method of adjusting dynamic range of electrical stimulation associated with a cochlear prosthesis system, the cochlear prosthesis system including an electrode array for $e_{i(1 \ldots N)}$ for stimulating the acoustic nerve, the method comprising:
   determining present electrode impedance values for an electrode in the array; including longitudinal tissue impedance $Z_L$ between electrodes in the array, and transversal tissue impedance $Z_T$; and
   adjusting at least one stimulation parameter for the electrode based, at least in part, on the present electrode impedance values, such that hearing sensation is not influenced due to a change between the present electrode impedance values and previous electrode impedance values,
   wherein adjusting the at least one stimulation parameter includes adjusting stimulation current level $I_i$ provided to the electrode as a function of longitudinal impedance $Z_L$ between electodes in the array and transversal tissue impedance $Z_T$.

2. The method according to claim 1, wherein the electrode array has a monopolar electrode configuration.

3. The method according to claim 1, wherein the electrode array has a bipolar electrode configuration.

4. The method according to claim 1, wherein the at least one stimulation parameter is selected from the group of parameters consisting of a Most Comfortable Level (MCL) parameter, a Threshold (THR) parameter, and electric dynamic range (DR), and combinations thereof.

5. The method according to claim 1, wherein adjusting the at least one stimulation parameter includes maintaining charge $Q_{Ti}$ that stimulates the acoustic nerve constant.

6. The method according to claim 1, wherein adjusting the at least one stimulation parameter includes adjusting pulse duration of stimulation current $I_i$ provided to the electrode.

7. The method according to claim 1, wherein adjusting the at least one stimulation parameter includes adjusting stimulation current level $I_i$ provided to the electrode upon an increase in longitudinal impedance $Z_L$ between the electrodes.

8. The method according to claim 1, further comprising repeating the steps of determining and adjusting for each electrode in the array.

9. The method according to claim 1, further comprising using a weighting to take into account spatial channel interaction.

10. The method according to claim 1, wherein the cochlear prosthesis system includes an audio processor for converting an incoming acoustic signal into an encoded signal, and a stimulation module for providing stimulation signals to the electrode array as a function of the encoded signal received from the audio processor, wherein the determining and adjusting is automatically performed within the audio processor or the stimulation module, or a combination thereof.

11. The method according to claim 1, further including coupling an external fitting processor to an audio processor of the cochlear prosthesis system, wherein the determining and adjusting is performed, at least in part, at the external fitting processor.

12. The method according to claim 1, further including providing a stimulation signal to the electrode based on the at least one stimulation parameter.

13. A cochlear prosthesis system comprising:
   an electrode array $e_{i(1 \ldots N)}$ configured to stimulate the acoustic nerve;
   an audio processor configured to convert an incoming acoustic signal into an encoded signal,
   a stimulator configured to provide stimulation signals to the electrode array as a function of the encoded signal received from the audio processor; and
   a dynamic range adjustment module configured to determine present electrode impedance values for an electrode in the array, including longitudinal tissue impedance $Z_L$ between electodes in the array, and transversal tissue impedance $Z_T$, and further configured to adjust at least one stimulation parameter for the electrode based, at least in part, on the present electrode impedance values, such that hearing sensation is not influenced due to a change between the present electrode impedance values and previous electrode impedance values, wherein the dynamic range adjustment module is configured to adjust stimulation current level $I_i$ provided to the electrode as a function of longitudinal impedance $Z_L$ between electrodes in the array and transversal tissue impedance $Z_T$.

14. The system according to claim 13, wherein the electrode array has a monopolar electrode configuration.

15. The method according to claim 13, wherein the electrode array has a bipolar electrode configuration.

16. The cochlear prosthesis system according to claim 13, wherein the dynamic range adjustment module is positioned, at least in part, within the audio processor or the stimulation module, or a combination thereof.

17. The cochlear prosthesis system according to claim 16, wherein the dynamic range adjustment module is configured to automatically adjust the at least one stimulation parameter.

18. The cochlear prosthesis system according to claim 13, further comprising an external fitting processor configured to operatively couple to the audio processor, wherein the dynamic range adjustment module is positioned, at least in part, within the external fitting processor.

19. The cochlear prosthesis system according to claim 13, wherein the at least one stimulation parameter is selected from the group of parameters consisting of a Most Comfortable Level (MCL) parameter, a Threshold (THR) parameter, and electric dynamic range (DR), and combinations thereof.

20. The cochlear prosthesis system according to claim 13, wherein the dynamic range module is configured to adjust the at least one stimulation parameter so as to maintain charge $Q_{Ti}$ that stimulates the acoustic nerve constant.

21. The cochlear prosthesis system according to claim 13, wherein the dynamic range adjustment module is configured to adjust the at least one stimulation parameter by adjusting current $I_{Ti}$ provided to the electrode.

22. The cochlear prosthesis system according to claim 13, wherein the dynamic range adjustment module is configured to adjust the at least one stimulation parameter by adjusting pulse duration of stimulation current $I_i$ provided to the electrode.

23. The cochlear prosthesis system according to claim 13, wherein the dynamic range adjustment module is configured to adjust stimulation current level $I_i$ provided to the electrode upon an increase in longitudinal impedance $Z_L$.

24. A cochlear prosthesis system comprising:
an electrode array $e_{i(1 \ldots N)}$ for stimulating the acoustic nerve;
means for determining present electrode impedance values for an electrode in the array, including longitudinal tissue impedance $Z_L$ between electrodes in the array, and transversal tissue impedance $Z_T$; and
means for adjusting at least one stimulation parameter for the electrode based, at least in part, on the present electrode impedance values, such that hearing sensation is not influenced due to a change between the present electrode impedance values and previous electrode impedance values,
wherein the means for adjusting the at least one stimulation parameter includes adjusting stimulation current level $I_i$ provided to the electrode as a function of longitudinal impedance $Z_L$ between electrdrodes in the array and transversal tissue impedance $Z_T$.

25. The system according to claim 24, wherein the electrode array has a monopolar electrode configuration.

26. The system according to claim 24, wherein the electrode array has a bipolar electrode configuration.

27. The cochlear prosthesis system according to claim 24, wherein the at least one stimulation parameter is selected from the group of parameters consisting of a Most Comfortable Level (MCL) parameter, a Threshold (THR) parameter, and electric dynamic range (DR), and combinations thereof.

28. The cochlear prosthesis system according to claim 24, wherein the means for adjusting the at least one stimulation parameter includes means for maintaining charge $Q_{Ti}$ that stimulates the acoustic nerve constant.

29. The cochlear prosthesis system according to claim 24, wherein the means for adjusting the at least one stimulation parameter includes means for adjusting pulse duration of stimulation current $I_i$ provided to the electrode.

30. The cochlear prosthesis system according to claim 24, wherein the means for adjusting the at least one stimulation parameter includes adjusting stimulation current level $I_i$ provided to the electrode upon an increase in longitudinal impedance $Z_L$.

31. The cochlear prosthesis system according to claim 24, further comprising:
an audio processor for converting an incoming acoustic signal into an encoded signal, and
a stimulation module for providing stimulation signals to the electrode array as a function of the encoded signal received from the audio processor, wherein the means for determining and the means for adjusting is automatically performed within the audio processor or the stimulation module, or a combination thereof.

32. The cochlear prosthesis system according to claim 24, further including:
an audio processor for converting an incoming acoustic signal into an encoded signal,
a stimulation module for providing stimulation signals to an electrode array as a function of the encoded signal received from the audio processor; and
an external fitting processor coupled to the audio processor, wherein the means for determining and means for adjusting is performed, at least in part, at the external fitting processor.

33. A non-transitory computer program product for adjusting dynamic range of electrical stimulation associated with a cochlear prosthesis system, the cochlear prosthesis system including an electrode array $e_{i(1 \ldots N)}$ for stimulating the acoustic nerve, the computer program product comprising a non-transitory computer usable medium having computer readable program code thereon, the computer readable program code comprising:
program code for determining present electrode impedance values for an electrode in the array, including longitudinal tissue impedance $Z_L$ between electrodes in the array, and transversal tissue impedance $Z_T$; and
program code for adjusting at least one stimulation parameter for the electrode based, at least in part, on the present electrode impedance values, such that hearing sensation is not influenced due to a change between the present electrode impedance values and previous electrode impedance values,
wherein the program code for adjusting the at least one stimulation parameter includes program code for adjusting stimulation current level $I_i$ provided to the electrode as a function of longitudinal impedance $Z_L$ between electrodes in the array and transversal tissue impedance $Z_T$.

34. The non-transitory computer program product according to claim 33, wherein the electrode array has a monopolar electrode configuration.

35. The non-transitory computer program product according to claim 33, wherein the electrode array has a bipolar electrode configuration.

36. The non-transitory computer program product according to claim 33, wherein the at least one stimulation parameter is selected from the group of parameters consisting of a Most Comfortable Level (MCL) parameter, a Threshold (THR) parameter, and electric dynamic range (DR), and combinations thereof.

37. The non-transitory computer program product according to claim 33, wherein the program code for adjusting the at least one stimulation parameter includes program code for maintaining charge $Q_{Ti}$ that stimulates the acoustic nerve constant.

38. The non-transitory computer program product according to claim 33, wherein the program code for adjusting the at least one stimulation parameter includes program code for adjusting pulse duration of stimulation current $I_I$ provided to the electrode.

39. The non-transitory computer program product according to claim 33, wherein the program code for adjusting the at least one stimulation parameter includes program code for adjusting stimulation current level $I_i$ provided to the electrode upon an increase in longitudinal impedance $Z_L$.

40. The non-transitory computer program product according to claim 33, wherein the cochlear prosthesis system further includes an audio processor for converting an incoming acoustic signal into an encoded signal, and a stimulation module for providing stimulation signals to an electrode array as a function of the encoded signal received from the audio processor, wherein the program code for determining and the program code for adjusting is automatically performed within the audio processor or the stimulation module, or a combination thereof.

41. The non-transitory computer program product according to claim 33, wherein the cochlear prosthesis system further includes an audio processor for converting an incoming acoustic signal into an encoded signal, a stimulation module for providing stimulation signals to an electrode array as a function of the encoded signal received from the audio processor, and an external fitting processor coupled to the audio processor, wherein the program code for determining and the program code for adjusting is performed, at least in part, at the external fitting processor.

* * * * *

UNITED STATES PATENT AND TRADEMARK OFFICE
CERTIFICATE OF CORRECTION

| | | |
|---|---|---|
| PATENT NO. | : 9,662,493 B2 | |
| APPLICATION NO. | : 14/660246 | |
| DATED | : May 30, 2017 | |
| INVENTOR(S) | : Mathias Kals et al. | |

It is certified that error appears in the above-identified patent and that said Letters Patent is hereby corrected as shown below:

In the Claims

In Column 11, Line 58 delete "for"

In Column 11, Line 62 replace ";" with ","

In Column 13, Line 10 replace "method" with "system"

Signed and Sealed this
Eighth Day of August, 2017

Joseph Matal
*Performing the Functions and Duties of the*
*Under Secretary of Commerce for Intellectual Property and*
*Director of the United States Patent and Trademark Office*